United States Patent [19]

O'Lenick, Jr.

[11] Patent Number: 5,196,499
[45] Date of Patent: Mar. 23, 1993

[54] TERMINAL SILICONE ESTER QUATERNARY COMPOUNDS

[75] Inventor: Anthony J. O'Lenick, Jr., Lilburn, Ga.

[73] Assignee: Siltech, Inc., Norcross, Ga.

[21] Appl. No.: 866,900

[22] Filed: Apr. 6, 1992

Related U.S. Application Data

[63] Continuation-in-part of Ser. No. 822,752, Jan. 21, 1992, Pat. No. 5,098,979.

[51] Int. Cl.$^5$ .............................................. C08G 77/06
[52] U.S. Cl. ........................................ 528/15; 528/26; 528/31; 528/28; 424/70; 548/951; 556/437; 427/387
[58] Field of Search .................. 528/26, 15, 31, 28; 427/387; 424/70; 548/951; 556/437

[56] References Cited

U.S. PATENT DOCUMENTS

| | | | |
|---|---|---|---|
| 4,083,856 | 4/1978 | Mendicino | 528/27 |
| 4,185,087 | 1/1980 | Morlino | 424/70 |
| 4,609,750 | 9/1986 | Kollmeier et al. | 556/419 |
| 4,800,077 | 1/1989 | O'Lenick, Jr. et al. | 424/70 |
| 5,073,619 | 12/1991 | O'Lenick, Jr. | 528/26 |
| 5,093,452 | 3/1992 | O'Lenick, Jr. | 528/25 |
| 5,098,979 | 3/1992 | O'Lenick, Jr. | 528/15 |

*Primary Examiner*—John C. Bleutge
*Assistant Examiner*—Margaret W. Glass

[57] ABSTRACT

The present invention relates to a series of novel silicone ester quaternary polymers which are substantive to fiber and provide outstanding softening properties to various fibers, hair and skin. The compounds of the present invention are prepared by the esterification of a terminal hydroxyl group which is present on a silicone polymer with monochloroacetic acid, and in a subsequent step, reacting the chloro ester so produced with a tertiary amine to produce the desired quaternary compound.

18 Claims, No Drawings

TERMINAL SILICONE ESTER QUATERNARY COMPOUNDS

RELATED APPLICATIONS

This application is a continuation in part of co-pending application Ser. No. 822,752 filed Jan. 21, 1992, which is now U.S. Pat. No. 5,098,979.

BACKGROUND OF THE INVENTION (1) Field of Invention

The present invention relates to a series of novel silicone ester quaternary polymers which are substantive to fiber and provide outstanding softening properties to various fibers, hair and skin. The compounds, because they contain a terminal ionizable cationic group provide the desired softening, lubrication, surface active, and foaming properties. Since the compounds of the present invention are high molecular weight silicone polymers, they have a high degree of oxidative stability, even at elevated temperatures. In addition, these compounds are non volatile. These combination of properties makes these polymers ideally suited for use in the textile, personal care and industrial cleaning markets.

The compounds of the present invention are prepared by the esterification of a terminal hydroxyl group which is present on a silicone polymer with monochloroacetic acid, and in a subsequent step, reacting the chloro ester so produced with a tertiary amine to produce the desired quaternary compound. In a preferred embodiment the hydroxy containing silicone polymer has been alkoxylated with ethylene oxide, propylene oxide, or mixtures thereof. The abitity to regulate the type of alkylene oxide and amount present in the silicone polymer results in a series of products ranging in water/oil solubility. The technology used to produce the compounds of the present invention is very flexible and allows us to prepare performance tailored molecules for specific applications.

Prior to this invention, silicone quaternary compounds contained a hydroxy propyl linkage between the pendant silicone molecule and the quaternary group. This linkage is placed in the molecule using a glycidyl epoxide silicone compound. Epoxide compounds of this type with their similarities to epichlorohydrin are expected to possess a high order of toxicity and be environmentally unfriendly. The compounds of the present invention are easily manufactured using essentially non-toxic raw materials and have improved surface active properties over other materials known heretofore. Additionally there was no known way to incorporate the alkylene oxide protion of the molecule, the selection of the correct amount of which allows for the synthesis of molecules having varied solubilities in many solvents.

(2) Object of the Invention

It is the object of the present invention to provide a series of novel terminal substituted ester containing silicone quaternary polymers, which have the quaternary group in the terminal position. These materials are substantive to the surface of fibers. This substantivity results in superior conditioning, softening, surface active and lubrication properties.

It is another objective of the current invention to provide terminal substituted ester quaternary silicone polymers which have very low volatility. Volatility is a major concern in formulating many products.

Still another object of the present invention is to provide a series of terminal cationic silicone polymers which have differing solubilities in water and organic solvents. This is achieved by selection of the hydroxy silicone polymer used as a raw material.

Still another object of the present invention is to provide a chloroacetate ester intermediate useful in the preparation of the compounds of the present invention. Application of the compounds of the invention can be from solvent, aqueous dispersion or solution, or applied neat in these processes.

The silicone polymers, suitable as raw materials, in a preferred embodiment, contain varying amounts of ethylene oxide, propylene oxide or butylene oxide or mixtures thereof. The presence of the oxide in the silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to a fiber. The ability to use temperature to deposit a lubricant, antistat onto a fiber offers a great advantage in cost effectiveness of fiber treatment, and results in less product usage.

(3) Description of the Arts and Practices

Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not chemically bonded the effect is very transient. The product is removed with one washing.

Many attempts have been made to overcome these problems and get a truly substantive non volatile product, which deposits on fiber efficiently. One approach has been to use hydrosilation technology to make alkoxylated silicone polymers, used as raw materials in this invention. These materials do not have the substantivity desired to make them suitable for use as fiber lubricants or antistats.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

THE INVENTION

1) Summary of the Invention

The present invention relates to a series of novel quaternary silicone polymers which contain an ester linkage group. These polymers have a terminal quaternary functional group present. The polymers by virtue of the pendent group deposit on fiber surfaces and form effective nonvolatile surface modifying finishes. The compounds of the present invention are substantive to cellulosic and synthetic fibers.

The products of the present invention are prepared by reaction of a terminal hydroxyl containing silicone polymer with chloroacetic acid to form a silicone chloroacetic ester. Subsequently, said ester is reacted with a tertiary amine to produce the compounds of the present invention.

The compounds of this invention are represented by the following formula;

$$R-Si(CH_3)_2-[O-Si(CH_3)(R^1)]_a-[O-Si(CH_3)_2]_c-O-Si(CH_3)_2-R$$

wherein;
R is $R'CH_2-C(O)O-(CH_2CH_2-O)_z-(CH_2CH(CH_3)O)_y-(CH_2CH_2-O)_x-(CH_2)_3-$;

a is an integer from 0 to 200;
c is an integer from 1 to 200, with the proviso that a+c is no more than 200;
$R^1$ is selected from the group consisting of $-(CH_2)_nCH_3$ and phenyl;
n is an integer from 0 to 10;
x, y and z are integers and are independently selected from 0 to 20;
R' is selected from the group consisting of;

$$-\overset{R^3}{\underset{R^5}{N}}-R^{4\oplus}\ Cl^{\ominus}$$

$R^3$, $R^4$, and $R^5$ are each independently alkyl having from 1 to 20 carbon atoms;

$$R^6\overset{O}{\underset{}{C}}NH(CH_2)_r\overset{R^7}{\underset{R^8}{N}}-^\oplus\ Cl^\ominus$$

$R^6$ is alkyl having from 6 to 20 carbon atoms
$R^7$ and $R^8$ are independently methyl or ethyl;
x, y, and z are independently integers each selected from 0 to 20;

r is an integer from 1 to 5;
and $$(CH_2)_v-\overset{\oplus}{\underset{CH_2CH_2OH}{N}}-\overset{}{\underset{}{C}}-R^9\ Cl^\ominus$$

wherein
$R^9$ is alkyl having from 6 to 20 carbon atoms;
v is an integer from 1 to 5.

The products of the present invention are prepared by reaction of a hydroxyl containing silicone polymer with a suitable halo acid selected most commonly chloracetic acid.

One method of placing preparing the reactive hydroxyl containing silicone polymer is to react silanic hydrogen containing polymer with allyl alcohol or allyl alcohol alkoxylate monomer. Procedures this reaction are well known to those skilled in the art.

EXAMPLES

TERMINAL SUBSTITUTED DIMETHICONE COPOLYOL COMPOUNDS

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856. These hydroxyl functional silicone compounds are subsequently esterified.

Compounds suitable for use as reactants in the preparation of the compounds of the present invention conform to the following structure;

$$H-R''-Si(CH_3)_2-[O-Si(CH_3)_2]_b-O-Si(CH_3)_2-R''-H$$

R'' is $-(CH_2)_3-O-(CH_2CH_2-O)_x-(CH_2(CH_3)CH-O)_y-(CH_2CH_2-O)_z-$ x, y and z are integers independently ranging from 0 to 20;
b is an integer from 1 to 200.

These materials are available from Siltech Inc. Norcross, Ga. and are marketed under the Siltech T series tradename.

| Example | Name | x | y | z | Molecular Weight |
|---|---|---|---|---|---|
| 1 | Siltech T 710 | 0 | 0 | 0 | 1,000 |
| 2 | Siltech T 706 | 5 | 1 | 0 | 6,000 |
| 3 | Siltech T 710 | 2 | 1 | 1 | 10,000 |
| 4 | Siltech T 750 | 10 | 5 | 10 | 50,000 |
| 5 | Siltech T 790 | 20 | 20 | 20 | 86,000 |

ESTERIFICATION

The reaction sequence for the preparation of the compounds of the present invention is as follows;

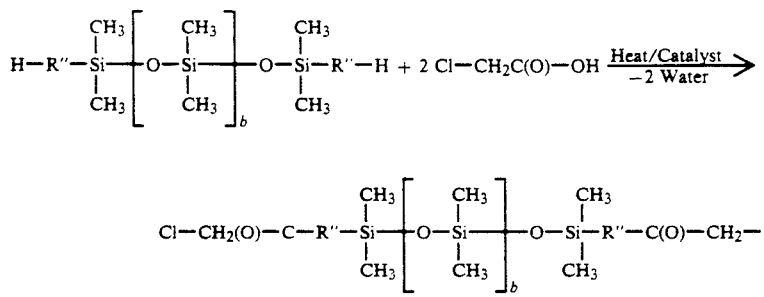

wherein
R" is

—(CH$_2$)$_3$—O—(CH$_2$CH$_2$—O)$_x$—(CH$_2$(CH$_3$)-
CH—O)$_y$—(CH$_2$CH$_2$—O)$_z$— x, y and z are integers independently ranging from 0 to 20;
b is an integer from 1 to 200.

GENERAL PROCEDURE

Place the indicated amount of the dimethicone copolyol produced by the example shown in a suitable vessel. Add the desired amount of catalyst as shown under good agitation and a nitrogen sparge. The specified amount of monochloroacetic acid is added. A molar excess of 0.1 to 0.5 of monochloroacetic acid is added. The temperature is held between 180–225 degrees C. for four to six hours. Reaction progress is monitored by acid value analysis, which is a measure of free chloroacetic acid.

Suitable catalysts are esterification catalysts including, sulfuric acid, p-toluene sulfonic, methane sulfonic, tin metal, zinc metal, titanium metal, organotitinates, organotin compounds, organo zinc compounds, zinc oxide and other esterification catalysts. The preferred catalysts is stannous oxylate. Chloroacetic acid is Cl—CH$_2$—C(O)—OH. It is also referred to as chloroethanoic acid, monochloroacetic acid, and MCA. It is an item of commerce.

Catalyst "A" below is stannous oxylate, Catalyst "B" is p-toluene sulfonic acid. Both are known esterification catalysts. Catalyst "B" was found to be more aggressive and result in a quicker reaction, however the color of the resulting product was darker. Catalyst "B" gave lighter colors but was somewhat slower. We found that using both the optimum catalyst system was attained.

| Example | Terminal Dimethicone Copolyol Example # | Grams | Grams of Chloro-Acetic Acid | Grams of Catalyst "A" | "B" |
|---|---|---|---|---|---|
| 6 | 1 | 500.0 | 100.0 | 0.4 | 0 |
| 7 | 2 | 3000.0 | 100.0 | 2 | 2 |
| 8 | 3 | 5000.0 | 100.0 | 0 | 4 |
| 9 | 4 | 25000.0 | 100.0 | 4 | 0 |
| 10 | 5 | 43000.0 | 100.0 | 2 | 2 |
| 11 | 1 | 500.0 | 50.0 | 0 | 4 |
| 12 | 2 | 3000.0 | 50.0 | 4 | 0 |
| 13 | 3 | 5000.0 | 50.0 | 0 | 4 |
| 14 | 4 | 25000.0 | 50.0 | 4 | 0 |
| 15 | 5 | 43000.0 | 50.0 | 2 | 2 |
| 16 | 1 | 500.0 | 40.0 | 0 | 4 |
| 17 | 2 | 3000.0 | 40.0 | 4 | 0 |

QUATERNARY REACTION SEQUENCE

All amine reactants are commercially available from Tomah Products Division of Exxon Chemicals Milton Wi., and Various other suppliers.

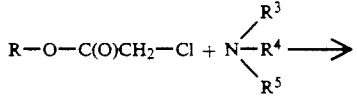

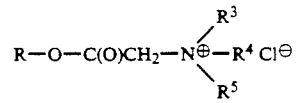

R contains the silicone portion of the molecule.

The following examples further illustrate the objects and advantages of this invention, though it should be understood that the various reactants and amounts thereof, reaction conditions, and other details are merely illustrative and should not be construed to unduly limit this invention.

AMINE REACTANT GROUP 1

The reactants are tertiary amines conforming to the following structure;

| | $R^3$ | | |
| | $R^4$—N—$R^5$ | | |
| Example Number | $R^3$ | $R^4$ | $R^5$ |
|---|---|---|---|
| 18 | C$_{10}$H$_{21}$ | CH$_3$ | CH$_3$ |
| 19 | C$_{12}$H$_{25}$ | CH$_3$ | CH$_3$ |
| 20 | C$_{14}$H$_{29}$ | CH$_3$ | CH$_3$ |
| 21 | C$_{16}$H$_{33}$ | CH$_3$ | CH$_3$ |
| 22 | C$_{18}$H$_{37}$ | CH$_3$ | CH$_3$ |
| 23 | C$_{20}$H$_{41}$ | CH$_3$ | CH$_3$ |
| 24 | C$_{10}$H$_{21}$ | C$_{16}$H$_{33}$ | CH$_3$ |
| 25 | C$_{12}$H$_{25}$ | C$_{18}$H$_{37}$ | CH$_3$ |
| 26 | C$_{14}$H$_{29}$ | C$_{20}$H$_{41}$ | CH$_3$ |
| 27 | C$_{16}$H$_{33}$ | C$_{10}$H$_{21}$ | CH$_3$ |
| 28 | C$_{18}$H$_{37}$ | C$_{12}$H$_{25}$ | CH$_3$ |
| 29 | C$_{20}$H$_{41}$ | C$_{14}$H$_{29}$ | CH$_3$ |
| 30 | C$_6$H$_{13}$ | C$_6$H$_{13}$ | C$_6$H$_{13}$ |
| 31 | C$_2$H$_5$ | CH$_3$ | C$_2$H$_5$ |
| 32 | C$_{10}$H$_{21}$ | C$_{10}$H$_{21}$ | C$_{10}$H$_{21}$ |

AMINE REACTANT GROUP 2

The reactants are amido tertiary amines conforming to the following structure;

$$R^6-C(O)N(H)-(CH_2)_3-\overset{R^7}{\underset{|}{N}}-R^8$$

| Example Number | $R^6$ | $R^7$ | $R^8$ |
|---|---|---|---|
| 33 | $C_5H_{11}$ | $CH_3$ | $CH_3$ |
| 34 | $C_7H_{15}$ | $CH_3$ | $CH_3$ |
| 35 | $C_9H_{19}$ | $CH_3$ | $CH_3$ |
| 36 | $C_{11}H_{23}$ | $CH_3$ | $CH_3$ |
| 37 | $C_{13}H_{27}$ | $CH_3$ | $CH_3$ |
| 38 | $C_{15}H_{31}$ | $CH_3$ | $CH_3$ |
| 39 | $C_{17}H_{35}$ | $CH_3$ | $CH_3$ |
| 40 | $C_{19}H_{39}$ | $CH_3$ | $CH_3$ |
| 41 | $C_{19}H_{39}$ | $CH_2CH_3$ | $CH_2CH_3$ |
| 42 | $C_{11}H_{23}$ | $CH_2CH_3$ | $CH_2CH_3$ |
| 43 | $C_5H_{11}$ | $CH_2CH_3$ | $CH_2CH_3$ |
| 44 | $C_5H_{11}$ | $CH_3$ | $CH_3$ |
| 45 | $C_7H_{15}$ | $CH_3$ | $CH_3$ |
| 46 | $C_9H_{19}$ | $CH_3$ | $CH_3$ |
| 47 | $C_{11}H_{23}$ | $CH_3$ | $CH_3$ |
| 48 | $C_{13}H_{27}$ | $CH_3$ | $CH_3$ |
| 49 | $C_{15}H_{31}$ | $CH_3$ | $CH_3$ |
| 50 | $C_{17}H_{35}$ | $CH_3$ | $CH_3$ |
| 51 | $C_{19}H_{39}$ | $CH_3$ | $CH_3$ |

AMINE REACTANT GROUP 3

The reactants are imidazoline compounds conforming to the following structure;

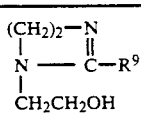

| Example Number | $R^9$ |
|---|---|
| 52 | $C_5H_{11}$ |
| 53 | $C_7H_{15}$ |
| 54 | $C_9H_{19}$ |
| 55 | $C_{11}H_{23}$ |
| 56 | $C_{13}H_{27}$ |
| 57 | $C_{15}H_{31}$ |
| 58 | $C_{17}H_{35}$ |
| 59 | $C_{19}H_{39}$ |

GENERAL REACTION PROCEDURE

The product of the present invention are generally prepared in aqueous solution or dispersion. The preferred concentration is about 50% solids. Additionally, alcohols such as methanol, ethanol, isopropanol, glycols such as ethylene glycol, propylene glycol, polypropylene glycol, polyethylenegylcol, hexylene glycol, and cyclomethicone can be added to improve clarity if desired.

To a suitable flask, equipped with a thermometer and agitator is added the specified amount of water. Next add the specified amount of the type of silicone reactant. Heat to 50° C. Next add the specified amount of the specified amine under good agitation. The reaction mass is heated to 85°-95° C. and held from between 5 and 15 hours. The reaction progress is monitored by % inorganic chloride, which approaches 98% of theoretical.

| | Amine Reactants | | Silicone Reactants | | Water |
|---|---|---|---|---|---|
| Example | Example | Grams | Example | Grams | Grams |
| 60 | 18 | 185.0 | 6 | 600.0 | 800.0 |
| 61 | 19 | 201.0 | 7 | 3,100.0 | 3,300.0 |
| 62 | 20 | 227.0 | 8 | 5,100.0 | 5,327.0 |

-continued

| | Amine Reactants | | Silicone Reactants | | Water |
|---|---|---|---|---|---|
| Example | Example | Grams | Example | Grams | Grams |
| 63 | 21 | 253.0 | 9 | 25,100.0 | 25,353.0 |
| 64 | 22 | 279.0 | 10 | 43,100.0 | 43,379.0 |
| 65 | 23 | 305.0 | 11 | 550.0 | 855.0 |
| 66 | 24 | 364.0 | 12 | 3,050.0 | 3,400.0 |
| 67 | 25 | 406.0 | 13 | 5,050.0 | 5,456.0 |
| 68 | 26 | 458.0 | 14 | 25,050.0 | 25,500.0 |
| 69 | 27 | 364.0 | 15 | 43,050.0 | 43,500.0 |
| 70 | 28 | 406.0 | 16 | 540.0 | 1,000.0 |
| 71 | 29 | 458.0 | 17 | 3,040.0 | 3,000.0 |
| 72 | 30 | 251.0 | 6 | 600.0 | 1,000.0 |
| 73 | 31 | 70.0 | 7 | 3,100.0 | 3,200.0 |
| 74 | 32 | 437.0 | 8 | 5,100.0 | 5,600.0 |
| 75 | 33 | 199.0 | 9 | 25,100.0 | 25,300.0 |
| 76 | 34 | 227.0 | 10 | 43,100.0 | 43,000.0 |
| 77 | 35 | 255.0 | 6 | 600.0 | 900.0 |
| 78 | 36 | 283.0 | 7 | 3,100.0 | 3,000.0 |
| 79 | 37 | 311.0 | 8 | 5,100.0 | 5,500.0 |
| 80 | 38 | 339.0 | 9 | 25,100.0 | 25,400.0 |
| 81 | 39 | 367.0 | 10 | 43,100.0 | 43,500.0 |
| 82 | 40 | 395.0 | 6 | 600.0 | 2,000.0 |
| 83 | 41 | 337.0 | 7 | 3,100.0 | 3,400.0 |
| 84 | 42 | 311.0 | 8 | 5,100.0 | 5,500.0 |
| 85 | 43 | 227.0 | 9 | 25,100.0 | 25,000.0 |
| 86 | 44 | 640.0 | 10 | 43,100.0 | 50,000.0 |
| 87 | 45 | 4,928.0 | 6 | 600.0 | 6,000.0 |
| 88 | 46 | 300.0 | 7 | 3,100.0 | 4,000.0 |
| 89 | 47 | 328.0 | 8 | 5,100.0 | 5,000.0 |
| 90 | 48 | 1,782.0 | 9 | 25,100.0 | 28,000.0 |
| 91 | 49 | 1,370.0 | 10 | 43,100.0 | 25,000.0 |
| 92 | 50 | 1,103.0 | 6 | 600.0 | 2,000.0 |
| 93 | 51 | 1,131.0 | 7 | 3,100.0 | 5,000.0 |
| 94 | 52 | 184.0 | 8 | 5,100.0 | 5,000.0 |
| 95 | 53 | 212.0 | 9 | 25,100.0 | 30,000.0 |
| 96 | 54 | 240.0 | 10 | 43,100.0 | 50,000.0 |
| 97 | 55 | 268.0 | 11 | 550.0 | 1,000.0 |
| 98 | 56 | 296.0 | 12 | 3,050.0 | 4,000.0 |
| 99 | 57 | 324.0 | 13 | 5,050.0 | 4,000.0 |
| 100 | 58 | 352.0 | 14 | 25,050.0 | 20,000.0 |
| 101 | 59 | 380.0 | 15 | 43,000.0 | 50,000.0 |

APPLICATIONS EVALUATION

The compounds of the present invention were found to be high foaming, conditioning and provided outstanding softening properties to hair, and textile fibers. Additionally they were found not to effect the rewet properties of cotton towels.

What is claimed is:

1. A silicone polymer which conforms to the following structure;

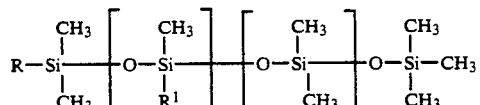

wherein;

R is

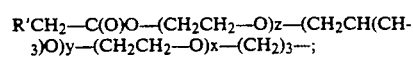

a is an integer from 0 to 200;

c is an integer from 1 to 200, with the proviso that a+c is no more than 200;

$R^1$ is selected from the group consisting of $-(CH_2)_nCH_3$ and phenyl;

n is an integer from 0 to 10;

x, y and z are integers and are independently selected from 0 to 20;

R' is selected from the group consisting of;

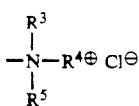

$R^3$, $R^4$, and $R^5$ are each independently alkyl having from 1 to 20 carbon atoms;

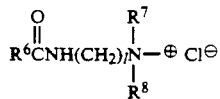

$R^6$ is alkyl having from 6 to 20 carbon atoms,
$R^7$ and $R^8$ are independently methyl or ethyl;
l is an integer from 1 to 5;
and

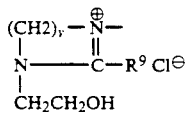

wherein
$R^9$ is alkyl having from 6 to 20 carbon atoms;
v is an integer from 1 to 5.

2. A silicone polymer of claim 1 wherein R' is;

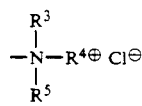

$R^3$, $R^4$, and $R^5$ are each independently alkyl having from 1 to 20 carbon atoms.

3. A silicone polymer of claim 1 wherein $^3R$ and $^4R$ are methyl and $R^5$ is alkyl having 18 carbon atoms.

4. A silicone polymer of claim 1 wherein R' is

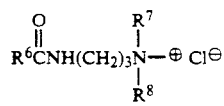

$R^6$ is alkyl having from 6 to 20 carbon atoms;
$R^7$ and $R^8$ are independently selected from the group consisting of methyl and ethyl.

5. A silicone polymer of claim 4 wherein $R^7$ and $R^8$ are methyl and $R^6$ is alkyl having 17 carbon atoms.

6. A silicone polymer of claim 4 wherein $R^7$ and $R^8$ are methyl and $R^6$ is alkyl having 11 carbon atoms.

7. A silicone polymer of claim 1 wherein R' is

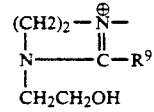

$R^9$ is alkyl having from 6 to 20 carbon atoms.

8. A silicone polymer of claim 7 wherein $R^9$ is alkyl having 17 carbon atoms.

9. A process for the treatment of fiber which comprises contacting the fiber with an effective conditioning amount of a silicone polymer which conforms to the following:

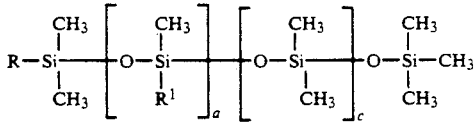

wherein;
R is

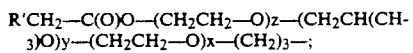

a is an integer from 0 to 200;
c is an integer from 1 to 200, with the proviso that a+c is no more than 200;
$R^1$ is selected from the group consisting of —$(CH_2)_nCH_3$ and phenyl;
n is an integer from 0 to 10;
x, y and z are integers and are independently selected from 0 to 20;
R' is selected from the group consisting of;

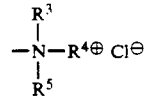

$R^3$, $R^4$, and $R^5$ are each independently alkyl having from 1 to 20 carbon atoms;

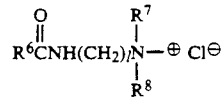

$R^6$ is alkyl having from 6 to 20 carbon atoms,
$R^7$ and $R^8$ are independently methyl or ethyl;
l is an integer from 1 to 5;
and

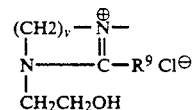

wherein
$R^9$ is alkyl having from 6 to 20 carbon atoms;
v is an integer from 1 to 5.

10. A process of claim 9 wherein R' is;

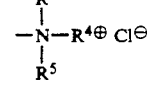

$R^3$, $R^4$, and $R^5$ are each independently alkyl having from 1 to 20 carbon atoms.

11. A process of claim 9 wherein $R^3$ and $R^4$ are methyl and $R^5$ is alkyl having 18 carbon atoms.

12. A process of claim 9 wherein R' is

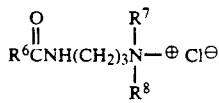

R[6] is alkyl having from 6 to 20 carbon atoms;
R[7] and R[8] are independently selected from the group consisting of methyl and ethyl.

13. A process of claim 12 wherein R[7] and R[8] are methyl and R[6] is alkyl having 17 carbon atoms.

14. A process of claim 12 wherein R[7] and R[8] are methyl and R[6] is alkyl having 11 carbon atoms.

15. A process of claim 9 wherein

R' is

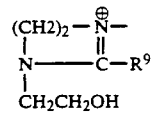

R[9] is alkyl having from 6 to 20 carbon atoms.

16. A process of claim 15 wherein R[9] is alkyl having 17 carbon atoms.

17. A process of claim 15 wherein R[9] is alkyl having 11 carbon atoms.

18. A chloro containing silicone ester intermediate conforming to the following structure;

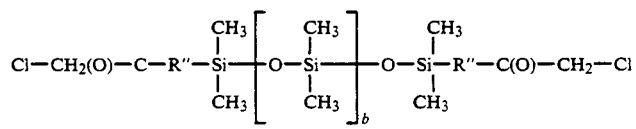

wherein
R'' is

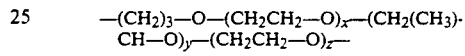

x, y and z are integers independently selected from 0 to 20;
b is an integer from 1 to 200.